United States Patent
Lee et al.

(10) Patent No.: US 9,205,058 B2
(45) Date of Patent: Dec. 8, 2015

(54) TAPE-TYPE FLUORINE PREPARATION USING BIODEGRADABLE POLYMER AND METHOD OF PREPARING THE SAME

(75) Inventors: Sang Ho Lee, Gwangju (KR); In Hwa Lee, Gwangju (KR)

(73) Assignee: INDUSTRY-ACADEMIC COOPERATION FOUNDATION, CHOSUN UNIVERSITY, Gwangju (KR)

( * ) Notice: Subject to any disclaimer, the term of this patent is extended or adjusted under 35 U.S.C. 154(b) by 0 days.

(21) Appl. No.: 14/129,584

(22) PCT Filed: Jun. 19, 2012

(86) PCT No.: PCT/KR2012/004828
§ 371 (c)(1),
(2), (4) Date: Dec. 27, 2013

(87) PCT Pub. No.: WO2013/002505
PCT Pub. Date: Jan. 3, 2013

(65) Prior Publication Data
US 2014/0112874 A1    Apr. 24, 2014

(30) Foreign Application Priority Data
Jun. 27, 2011    (KR) .................. 10-2011-0062345

(51) Int. Cl.
| | | |
|---|---|---|
| *A61Q 11/00* | (2006.01) | |
| *A61K 6/00* | (2006.01) | |
| *A61K 9/70* | (2006.01) | |
| *A61K 9/22* | (2006.01) | |
| *A61L 15/58* | (2006.01) | |
| *A61K 47/32* | (2006.01) | |
| *A61K 47/38* | (2006.01) | |
| *A61C 19/06* | (2006.01) | |
| *A61K 9/00* | (2006.01) | |

(52) U.S. Cl.
CPC ............. *A61K 9/7007* (2013.01); *A61C 19/063* (2013.01); *A61K 9/0053* (2013.01); *A61K 47/32* (2013.01); *A61K 47/38* (2013.01)

(58) Field of Classification Search
CPC . A61K 9/2054; A61K 9/7007; A61K 9/0056; A61K 9/006; A61L 15/58; A61Q 11/00
USPC .............................. 424/443, 49, 426, 52, 468
See application file for complete search history.

(56) References Cited

U.S. PATENT DOCUMENTS

| | | | | |
|---|---|---|---|---|
| 5,624,960 | A * | 4/1997 | Wenzel et al. ................. | 514/565 |
| 6,096,328 | A * | 8/2000 | Sagel et al. .................... | 424/401 |
| 2004/0062724 | A1 | 4/2004 | Moro | |
| 2006/0062743 | A9 * | 3/2006 | Nathoo ........................... | 424/49 |
| 2006/0099550 | A1 * | 5/2006 | Faasse et al. .................. | 433/215 |
| 2007/0166244 | A1 * | 7/2007 | Ghosh et al. ................... | 424/49 |
| 2008/0286317 | A1 * | 11/2008 | Botzem et al. ................ | 424/401 |
| 2011/0142942 | A1 * | 6/2011 | Schobel et al. ............... | 424/489 |

FOREIGN PATENT DOCUMENTS

| | | |
|---|---|---|
| KR | 10-2003-0059552 | 7/2003 |
| KR | 10-2004-0090061 | 10/2004 |
| KR | 10-0873274 | 12/2008 |
| KR | 10-2009-0092520 | 9/2009 |

OTHER PUBLICATIONS

Kim et al. Machine Translation of KP 10-2009-0092520 (Sep. 1, 2009). Date retrieved: Jan. 8, 2015.*

* cited by examiner

*Primary Examiner* — Frederick Krass
*Assistant Examiner* — Tracy Liu
(74) *Attorney, Agent, or Firm* — Lex IP Meister, PLLC

(57) ABSTRACT

Provided are a tape-type fluorine preparation using a biodegradable polymer and a method of preparing the same, and preferably, a tape-type fluorine preparation which is attached to teeth to gradually release fluorine, thereby maintaining a suitable fluorine concentration in an oral cavity, and self-degraded after a certain amount of time, and a method of preparing the same. The tape-type fluorine preparation includes a pressure-sensitive adhesive sheet containing fluorine and capable of being attached to teeth, and the pressure-sensitive adhesive sheet is formed of a biodegradable hydrophilic polymer in an oral cavity to reduce a rate at which the fluorine is released.

2 Claims, 4 Drawing Sheets

TAPE-TYPE FLUORINE PREPARATION USING BIODEGRADABLE POLYMER AND METHOD OF PREPARING THE SAME

TECHNICAL FIELD

The present invention relates to a tape-type fluorine preparation using a biodegradable polymer and a method of preparing the same, and more particularly, to a tape-type fluorine preparation, which is attached to teeth and gradually releases fluorine to maintain a suitable fluorine concentration in an oral cavity, and then is self-degraded after a certain amount of time, and a method of preparing the same.

BACKGROUND ART

It is well known that fluorine ions are applied to tooth tissue to provide reinforcement, and dental materials in which fluorine ion-releasing materials are blended are already being used to prevent and inhibit caries.

As a representative method to prevent dental caries, a method of caring a dental plaque, a method of utilizing fluorine, a sealant method, or a dietary control method. Among them, starting from the research disclosed in 1938 by Dean, relating to a concentration of fluorine ions in drinks is inversely proportional to the occurrence of caries, a great amount of research using fluorine to prevent dental caries has been conducted.

For example, particularly, in Japanese Laid-Open Patent Application No. sho 57-88106, a dental material containing a homopolymer of (meth)acrylic acid fluoride or a copolymer of (meth)acrylic acid fluoride and a (meth)acrylic acid lower alkylester as a fluorine ion-sustained release material is disclosed, and in Japanese Laid-Open Patent Application No. Hei 7-101819, a dental resin composition containing a specific fluorine-containing phosphazene monomer as a fluorine ion-sustained release material is disclosed.

Fluorine prevents tooth decalcification and enhances remineralization, thereby preventing caries in healthy teeth or teeth in which caries has occurred. That is, when fluorine ions are applied to an enamel of a tooth surface and substituted with a hydroxide group of an enamel hydroxyapatite crystal, they can stabilize the apatite crystal, and thus increase acid resistance of teeth, thereby preventing dental caries. When the fluorine is administered during formation of enamel, a concentration of fluorine ions of the enamel is increased, the acid resistance is increased, and the occurrence of caries is inhibited. Moreover, as a subsidiary means, fluorine application is developed.

The fluorine application is used as a method of preventing caries or treating sensitive teeth by increasing the concentration of fluorine ions of the enamel.

The fluorine application is performed using a fluorine gel or a fluorine varnish. However, since it is noted that the fluorine gel is hydrophilic, has a short contact time with teeth, presents a risk when swallowed during application, and discolors and erodes previous esthetic restoration, recently, the use of fluorine varnish has been increasing.

In case of the fluorine varnish, the first generation varnish, Duraphat (Colgate-Palmolive, USA), was first developed and commercially available in Europe in the late 1960s, and an individually packed third generation fluorine varnish has since been developed. The fluorine varnish can allow fluorine to bind to a natural resin having high adhesion to teeth to contact a high concentration of fluorine with the teeth for a long time, thereby increasing an opportunity to accumulate calcium fluoride on a surface of the teeth, and thus it has a short application time, and a simple technique.

However, the fluorine varnish has a resin as a main component, and thus causes inconveniences such as temporary discoloration of teeth, an unpleasant flavor, and sticky texture in application. In addition, the fluorine varnish does not stay attached to the teeth surface for a long time and is easily removed due to saliva or food, and thus a suitable fluorine concentration cannot be maintained in an oral cavity for a long time.

DISCLOSURE

Technical Problem

The present invention is directed to providing a bio-affinitive tape-type fluorine preparation, which attaches to teeth to slowly release fluorine for a long time, thereby providing high anti-cariogenicity to tooth tissue, and is self-degraded after a certain amount of time, and a method of preparing the same.

Technical Solution

One aspect of the present invention provides a tape-type fluorine preparation, which includes a pressure-sensitive adhesive sheet containing fluorine and attachable to teeth. The pressure-sensitive adhesive sheet is formed of a biodegradable hydrophilic polymer in an oral cavity to reduce a rate at which the fluorine is released.

The hydrophilic polymer is at least one of polyvinyl alcohol and methyl cellulose.

The pressure-sensitive adhesive sheet contains a pressure-sensitive adhesive to enhance adhesion to teeth.

A pressure-sensitive adhesive layer capable of attaching to a surface of the teeth is formed on one surface of the pressure-sensitive adhesive sheet.

Another aspect of the present invention provides a method of preparing a tape-type fluorine preparation, which includes applying a solvent to a biodegradable hydrophilic polymer and stirring the mixture to obtain a polymer solution (first operation), adding polyethylene glycol to the polymer solution and stirring the resulting solution (second operation), adding a fluorine compound to the polymer solution and stirring the resulting solution (third operation), and plasticizing the polymer solution in a film type (fourth operation).

The hydrophilic polymer is at least one of polyvinyl alcohol and methyl cellulose.

In the third operation, a pressure-sensitive adhesive is further added to enhance the adhesion to the teeth.

Advantageous Effects

According to the present invention, when a tape-type fluorine preparation is attached to teeth, fluorine is gradually released for a long time, and thus a suitable fluorine concentration can be maintained in an oral cavity for a long time. Thus, high anti-cariogenicity is provided to tooth tissue.

In addition, the tape-type fluorine preparation can be useful as a bio-affinitive and environmentally friendly oral medication by being removed by self-degradation after a certain amount of time.

MODES OF INVENTION

Figure 1:
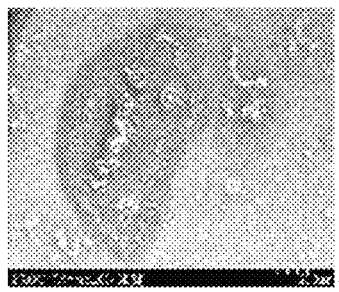
FIGS. 1 to 9 are images showing changes of a fluorine preparation in artificial saliva according to time.
Figure 2:
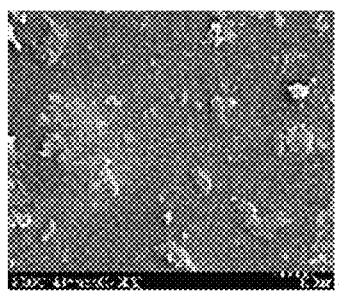
Figure 3:
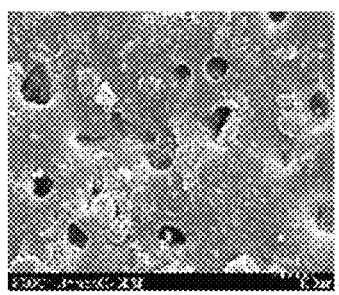
Figure 4:
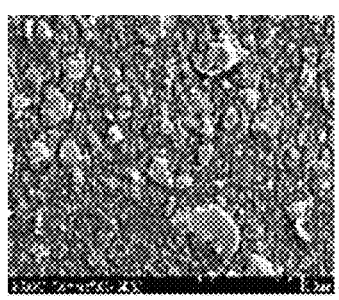
Figure 5:
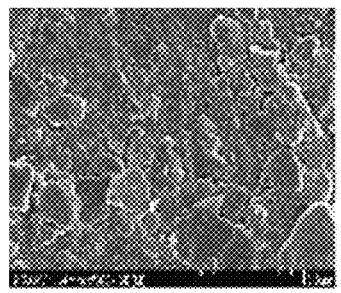
Figure 6:
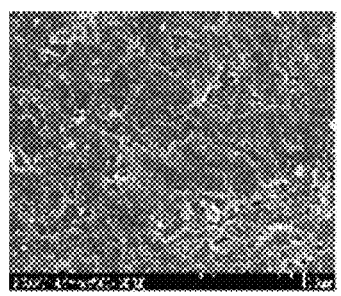
Figure 7:
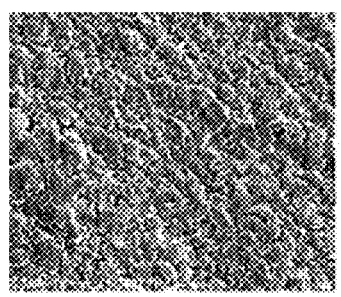
Figure 8:
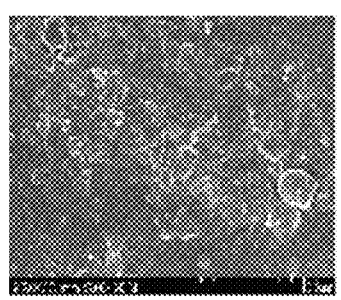
Figure 9:
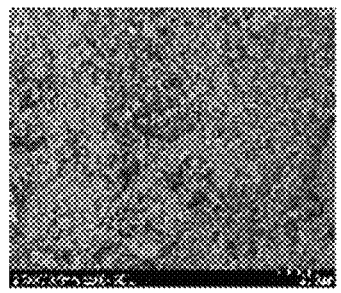

Hereinafter, a tape-type fluorine preparation using a biodegradable polymer and a method of preparing the same will be described in detail with reference to exemplary Examples.

The fluorine preparation includes a pressure-sensitive adhesive sheet capable of attaching to teeth. The pressure-sensitive adhesive sheet is formed in a tape-type thin film. The pressure-sensitive adhesive sheet may maintain a strength and an elasticity, and have a thickness that can closely fit to a curved surface of the teeth. To this end, the pressure-sensitive adhesive sheet may have a thickness of 10 to 30 μm.

The pressure-sensitive adhesive sheet contains a certain amount of fluorine. A preferable fluorine content is 5 to 15 wt % of the total weight of the fluorine preparation.

In the present invention, fluorine is dispersed in the pressure-sensitive adhesive sheet. The pressure-sensitive adhesive sheet can continuously release fluorine into an oral cavity for a long time by reducing a rate of fluorine release, and is formed of a biodegradable hydrophilic polymer.

The hydrophilic polymer is a biodegradable material, which is not harmful to the human body and serves as a hydrophilic receptor. For example, as the hydrophilic polymer, polyvinyl alcohol or methyl cellulose is used. In addition, a mixture of polyvinyl alcohol and methyl cellulose is used.

The polyvinyl alcohol may be one that is partially or completely saponified and has a molecular weight of 500 to 1700, and preferably one that is completely saponified and has a molecular weight of 1700 Mv.

In addition, as the methyl cellulose, sodium carboxymethyl cellulose (sodium CMC) may be used. The sodium CMC is a bio-affinitive material whose bio-stability has been confirmed. The pressure-sensitive adhesive sheet using such sodium CMC is closely attached to a tooth surface, has no stickiness, is less unpleasant, and is biodegraded in saliva. The methyl cellulose has different physical properties according to viscosity. The methyl cellulose suitable for the present invention has a viscosity of 400 centipoises (cp) in terms of tensile strength and elongation.

When the polyvinyl alcohol and the methyl cellulose are mixed, in terms of the tensile strength and the elongation, a weight ratio of polyvinyl alcohol to methyl cellulose may be 3:2 to 5.

Other than the above-described hydrophilic polymer, one or at least two of a polyalkylvinylester-maleic acid copolymer (PVM/MA copolymer), a polyacrylic acid, a polyvinylpyrrolidone-vinylacetate copolymer (PVP/VA copolymer), a polyvinylpyrrolidone (PVP), a polyquaternium-11, a polyquaternium-39, a gelatin or an alginate such as sodium alginate may be used.

A content of the hydrophilic polymer may be 50 to 70 wt % of the total weight of the fluorine preparation.

In addition, the pressure-sensitive adhesive sheet may contain a plasticizer to enhance physical properties of the hydrophilic polymer. As the plasticizer, polyethyleneglycol, propyleneglycol, or glycerin may be used. To have suitable flexibility, a content of the plasticizer may be 5 to 15 wt % of the total weight of the fluorine preparation.

Meanwhile, the pressure-sensitive adhesive sheet may contain a pressure-sensitive adhesive to increase adhesion to teeth. A content of the pressure-sensitive adhesive may be 10 to 30 wt % of the total weight of the fluorine preparation. As the pressure-sensitive adhesive, a carboxyvinyl polymer may be applied. The pressure-sensitive adhesive may be contained in the pressure-sensitive adhesive sheet in the operation of plasticization of the pressure-sensitive adhesive sheet.

In addition, when the pressure-sensitive adhesive is applied on one surface of the pressure-sensitive adhesive sheet, the adhesion of the pressure-sensitive adhesive sheet to teeth may be improved by forming a pressure-sensitive adhesive layer.

Hereinafter, a method of preparing the above-described tape-type fluorine preparation will be described.

A method of preparing the fluorine preparation according to the present invention includes applying a solvent to a biodegradable hydrophilic polymer and stirring the mixture to obtain a polymer solution (first operation), adding a plasticizer to the polymer solution and stirring the resulting solution (second operation), adding a fluorine compound to the polymer solution and stirring the resulting solution (third operation), and plasticizing the polymer solution in a film form (fourth operation).

First, a polymer solution is obtained by applying a solvent to a hydrophilic polymer and stirring the resulting mixture for 10 to 20 minutes. The hydrophilic polymer is as described above. The hydrophilic polymer is mixed at 10 to 25 parts by weight with respect to 100 parts by weight of the solvent. As the solvent, distilled water or an alcohol such as ethanol and methanol may be used. As the alcohol solvent, in addition to ethanol or methanol, n-propanol, isopropanol, n-butanol, isobutanol, amylalcohol, 3-pentanol, n-hexanol, methylaminealcohol, 2-ethylbutanol, n-heptanol, 2-heptanol, 3-heptanol, n-octanol, 2-octanol, 2-ethylhexanol or 3,3,5-trimethylhexanol may also be used.

Subsequently, a plasticizer is added to the polymer solution, and the resulting mixture is stirred for 10 to 20 minutes. The plasticizer is as described above. The plasticizer is added at 1 to 10 parts by weight with respect to 100 parts by weight of the polymer solution.

In addition, the fluorine compound is added to the polymer solution to which the plasticizer is added, and then the mixed solution is stirred for 10 to 20 minutes. Here, the fluorine compound is added at 1 to 10 parts by weight with respect to 100 parts by weight of the polymer solution. For example, the fluorine compound is sodium fluoride, potassium fluoride, tin fluoride, sodium monofluorophosphate, or calcium monofluorophosphate.

A pressure-sensitive adhesive may be further added to the polymer solution in addition to the fluorine compound. The pressure-sensitive adhesive may be included at 2 to 20 parts by weight with respect to 100 parts by weight of the polymer solution.

Subsequently, the polymer solution in which the plasticizer and the fluorine compound are dissolved is bathed at 80° C. for 10 to 20 minutes, thereby forming a sol. Then, the sol is plasticized using a planar film manufacturer in a tape-type pressure-sensitive adhesive sheet to have a thickness of approximately 10 to 30 μm. The plasticized pressure-sensitive adhesive sheet is dried in a drier, thereby obtaining the fluorine preparation of the present invention.

As described above, in the present invention, as fluorine is contained in the pressure-sensitive adhesive sheet formed of a polymer whose stability in a human body is proved to gradually release the fluorine, and the adhesion to teeth is improved, the fluorine is slowly released while attached to the teeth for a long time, and thus has an excellent effect.

Hereinafter, the fluorine preparation of the present invention will be described with reference to Examples. However, the following Examples are merely provided to describe the present invention in detail, and the scope of the present invention is not limited to the following Examples.

EXAMPLES

A polymer solution was prepared by adding 15 g of a hydrophilic polymer to 85 g of distilled water and stirring the resulting solution at 80° C. for 2 hours. In addition, 3 g of polyethylene glycol was added to the polymer solution, and the resulting solution was stirred at 80° C. for 2 hours. In addition, 2.5 g of sodium fluoride and 7 g of a carboxyvinyl polymer were added, stirred, and then bathed at 80° C. for 115 minutes, thereby forming a sol. Moreover, the sol was plasticized into a tape-type pressure-sensitive adhesive sheet using a planar film manufacturer, and dried at 60° C. for 24 hours, thereby preparing a fluorine preparation.

In this Example, as the hydrophilic polymer, various kinds of fluorine preparations were prepared using polyvinyl alcohol (PVA) or sodium CMC alone, and a mixture of a PVA and sodium CMC. When the PVA and CMC were mixed, a content of the sodium CMC was changed.

<1. Experiment for Measuring Tensile Strength and Elongation of Polymer>

To search for a polymer suitable for the fluorine preparation, the tensile strength and elongation of the polymer were measured.

A glass plate for manufacturing a film was manufactured with a common glass having a size of 400 mm×400 mm×5 mm, and formed in the form of a film using a YBA-7 applicator produced by YOSHIMITSU capable of controlling a thickness to 12.5 to 250 μm and an applicator produced by SHEEN capable of controlling a thickness to 0.1 to 10 mm. Thicknesses of specimens taken from top, middle and bottom parts of the film were measured five times or more using dial calipers (Mitutoyo, Japan) having a 0.25 μm, and then an average value thereof was obtained.

In this experiment, the tensile strength and elongation were measured using the fluorine preparation of Example as a sample according to a tensile test method for a plastic film and sheet (KS M 3054). The experiment was performed with respect to 5 specimens under conditions of a temperature of 20 to 25° C., and a relative humidity of 50±5%. Each specimen was cut to a size of 20 mm×200 mm×10 mm (width× length×grip distance), and the tensile strength and elongation of the specimen were measured using UTM on which a 200N-load cell was equipped (Shimadzu, Japan).

First, the tensile strength and elongation according to the kind of the PVA were examined. The PVA was tested by changing a saponification value and a molecular weight. That is, as PVAs, one that is partially saponified and has a molecular weight of 500 (P-05A), one that is partially saponified and has a molecular weight of 1700 (P-17A), one that is partially saponified and has a molecular weight of 2000 (P-20A), and one that is partially saponified and has a molecular weight of 1700 (F-17A) were used. Experimental results are shown in Table 1.

TABLE 1

| Cate-gory | Tensile strength (MPa) | | | Elongation (%) | | | Thickness (μm) | | |
| --- | --- | --- | --- | --- | --- | --- | --- | --- | --- |
| | Min. | Max. | Mean | Min. | Max. | Mean | Min. | Max. | Mean |
| P-05A | 15.1 | 29.4 | 20.2 | 8.4 | 23.6 | 15.1 | 0.023 | 0.029 | 27 |
| P-17A | 23.3 | 42.4 | 32.1 | 21.3 | 84.1 | 60.6 | 0.031 | 0.037 | 30 |
| P-20A | 31.9 | 47.7 | 38.6 | 26.9 | 90.1 | 51.2 | 0.025 | 0.027 | 26 |
| F-17A | 45.7 | 55.3 | 51.1 | 2.9 | 3.5 | 3.1 | 0.040 | 0.043 | 40 |

Referring to the results shown in Table 1, F-17A PVA was the most excellent in the tensile strength and elongation, and thus it was seen that a thickness of the F-17A PVA was easily controlled.

Afterward, the tensile strength and elongation according to a viscosity of sodium CMC were examined. The sodium CMC having a viscosity of 15, 400, or 1500 cp was used. Experimental results are shown in Table 2.

TABLE 2

| Category | Tensile strength (MPa) | Elongation (%) | Thickness (μm) |
| --- | --- | --- | --- |
| 15 cp | 15.44 | 26.42 | 9 |
| 400 cp | 20.92 | 49.31 | 33 |
| 1500 cp | 21.70 | 41.98 | 76 |

Referring to Table 2, as the viscosity of the sodium CMC increased, the tensile strength increased, but the elongation was the highest at 400 cp sodium CMC. The tensile strength and elongation were greatly affected by the thickness, but as the thickness increased, variations of the tensile strength and elongation were not proportional to that of the thickness. This means that the tensile strength and elongation were affected by the thickness, but not greatly affected.

In addition, in the process of manufacturing a sodium CMC film having a viscosity of 15, 400 or 1500 cp, it was seen that the films having viscosities of 15 and 400 cp were easily manufactured, but a thickness of the 1500 cp film was difficult to control and decreased in transparency during drying because of high viscosity. Though the film manufactured of 1500 cp CMC had a high tensile strength, it had almost no difference in tensile strength from the 400 cp film, and the elongation was higher with the 400 cp film. This means that the fluorine preparation was formed of 400 cp CMC, which was more efficient.

From the above-described experimental results, it was seen that a fluorine preparation having excellent properties could be prepared using F-17A PVA and CMC having a viscosity of 400 cp.

<2. Experiment for Measuring Tensile Strength and Elongation of Fluorine Preparation>

The tensile strength and elongation were measured using the fluorine preparation prepared in Example as a sample. The first sample used PVA alone as a hydrophilic polymer, the second to fourteenth samples used a mixture of PVA and sodium CMC as a hydrophilic polymer, and the fifteenth sample used sodium CMC as a hydrophilic polymer. In addition, when the PVA and the sodium CMC were mixed, they were shown in a weight ratio of the CMC to the PVA.

The PVA used in the preparation of the fluorine preparation was completely saponified and had a molecular weight of 1700 (F-17A), and the SCS had a viscosity of 400 cp. The tensile strength and elongation were measured by a method for a tensile test of a plastic film and sheet (KS M 3054). The tensile strength and elongation according to the test samples are shown in Table 3.

TABLE 3

| | Tensile strength (MPa) | | | Elongation (%) | | |
| --- | --- | --- | --- | --- | --- | --- |
| Category | Min. | Max. | Mean | Min. | Max. | Mean |
| First sample (PVA alone) | 58.44 | 61.32 | 59.88 | 130.94 | 149.05 | 139.99 |
| Second sample (PVA + CMC 1%) | 45.66 | 67.14 | 53.41 | 103.35 | 165.09 | 123.38 |
| Third sample (PVA + CMC 3%) | 43.09 | 60.47 | 52.47 | 71.04 | 132.35 | 105.18 |

TABLE 3-continued

| Category | Tensile strength (MPa) | | | Elongation (%) | | |
|---|---|---|---|---|---|---|
| | Min. | Max. | Mean | Min. | Max. | Mean |
| Fourth sample (PVA + CMC 5%) | 34.12 | 49.24 | 41.68 | 59.09 | 125.04 | 92.06 |
| Fifth sample (PVA + CMC 8%) | 37.58 | 44.73 | 41.14 | 70.23 | 104.91 | 80.81 |
| Sixth sample (PVA + CMC 10%) | 37.36 | 44.25 | 40.76 | 92.67 | 121.27 | 109.53 |
| Seventh sample (PVA + CMC 15%) | 34.72 | 43.41 | 39.50 | 112.04 | 169.37 | 149.62 |
| Eighth sample (PVA + CMC 20%) | 29.25 | 33.33 | 31.96 | 103.87 | 134.06 | 122.86 |
| Ninth sample (PVA + CMC 25%) | 26.67 | 29.58 | 28.06 | 96.84 | 125.73 | 114.80 |
| Tenth sample (PVA + CMC 30%) | 21.65 | 25.51 | 23.78 | 54.51 | 114.76 | 85.08 |
| Eleventh sample (PVA + CMC 35%) | 21.13 | 22.10 | 21.78 | 33.84 | 79.88 | 47.26 |
| Twelfth sample (PVA + CMC 40%) | 19.27 | 20.42 | 19.96 | 33.06 | 39.50 | 36.19 |
| Thirteenth sample (PVA + CMC 45%) | 19.09 | 20.25 | 19.74 | 42.36 | 53.88 | 48.06 |
| Fourteenth sample (PVA + CMC 50%) | 17.62 | 21.74 | 19.42 | 30.81 | 61.92 | 46.95 |
| Fifteenth sample (CMC alone) | 12.24 | 17.74 | 15.44 | 21.21 | 34.24 | 26.42 |

Referring to the results shown in Table 3, when PVA was used alone as a hydrophilic polymer, the tensile strength and elongation were higher than those when CMC was used alone, or PVA was mixed with sodium CMC. In addition, when sodium CMC was mixed at 10 to 25% in the PVA, the elongation was relatively higher, and particularly, when sodium CMC was mixed at 15% in PVA, the elongation was higher than that when PVA (PVA) was used alone.

<3. Fluorine Releasing Experiment>

To examine an effect of releasing fluorine of the fluorine preparation prepared in Example (the tenth sample in Table 3), a fluorine releasing test was performed using a conventional gel-type fluorine gel (topex, sultan, USA), and a varnish-type fluorine varnish (cavityshield, ominii pharmaceuticals, USA). A change in an average fluorine concentration in saliva according to time was shown as a graph in FIG. 10, and the results are summarized in Table 4.

rine, "F-varnish" refers to varnish-type fluorine, and "F-tape" refers to a fluorine preparation, which is the tenth sample of Table 3.

<4. Biodegradation Test>

To examine degradation of the fluorine preparation prepared in Example (the tenth item of Table 3) in an oral cavity, the fluorine preparation was dipped in artificial saliva. As the artificial saliva, a solution containing 50% saturated 0.1 M lactic acid saturated with 50% calcium phosphate tribasic (Sigma, USA) and 0.2% Carbopol (#907, BF Goodrich, USA) and adjusted to pH 4.0 was used.

Before and after the experiment, every 20 seconds, a change in microstructure of the fluorine preparation was photographed using a scanning electron microscope, and the results are shown in FIGS. 1 to 9.

FIG. 1 is an image of a fluorine preparation before the experiment, and FIGS. 2 to 9 are images sequentially taken every 20 seconds after the experiment.

Referring to FIGS. 1 to 9, the fluorine preparation of the present invention was confirmed to have a condensed tissue before dissolution. In addition, after 40 seconds, pores started to form, and as time passed, it was confirmed that the tissue was gradually degraded.

Subsequently, to examine a degradation time according to the kind of the polymer, four kinds of fluorine preparations were tested.

As a sample used in the test, the fourth sample (PVA 15%+sodium CMC 5%, the seventh sample (PVA 15%+sodium CMC 15%), the ninth sample (PVA 15%+sodium CMC 25%), and the fourteenth sample (PVA 15%+sodium CMC 50%) shown in Table 3 were used.

To confirm a degree of biodegradation under aerobic composting conditions of the four kinds of samples, the test was performed by a method of measuring an amount of carbon oxide generated in the aerobic composting by applying KS M 3100-1:2003 (measurement of aerobic biodegradation degree and decay scheme of plastic under compost-composting conditions—first part: a quantitative method of generated carbon dioxide by titration).

An amount of accumulated carbon dioxide generated in each test under aerobic composting conditions and an accu-

TABLE 4

| | Elapsed time | | | | | | |
|---|---|---|---|---|---|---|---|
| Category | 1 hr | 3 hr | 5 hr | 7 hr | 1 day | 2 days | 3 days |
| Fluorine gel | 8.85 ± 12.44* | 3.14 ± 3.84* | 0.97 ± 0.70* | 0.59 ± 0.30* | 0.15 ± 0.08 | 0.17 ± 0.07 | 0.17 ± 0.07 |
| Fluorine varnish | 16.49 ± 8.47* | 10.14 ± 9.57* | 1.98 ± 1.59* | 0.85 ± 0.48* | 0.14 ± 0.06 | 0.17 ± 0.08 | 0.20 ± 0.10 |
| Tenth sample (fluorine tape) | 1.09 ± 0.41* | 0.72 ± 0.26* | 0.64 ± 0.30* | 0.72 ± 0.58* | 0.21 ± 0.11 | 0.20 ± 0.16 | 0.25 ± 0.08 |

[An asterisk (*) indicates a significant difference in fluoride concentration between the baseline and each measuring time ($p < 0.05$)]

Figure 10:
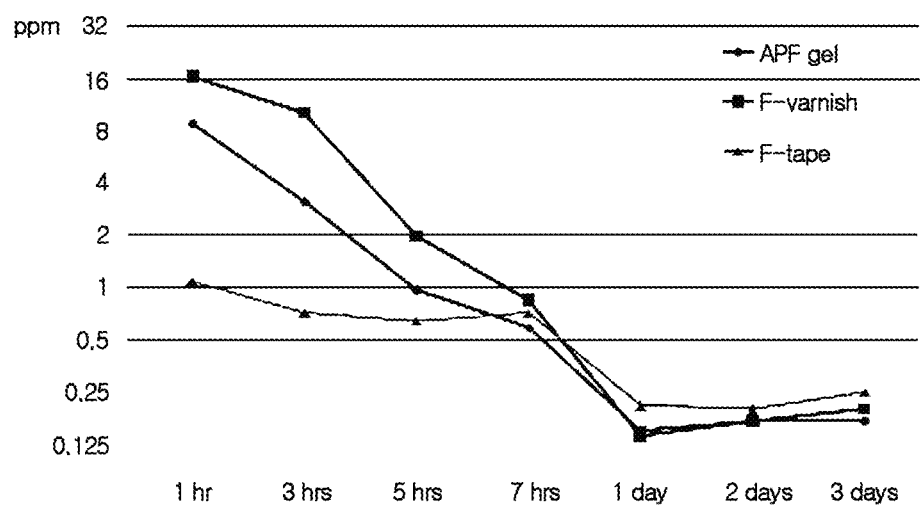
FIG. 10 is a graph showing a change in average fluorine concentration in saliva.

Referring to FIG. 10 and Table 4, the fluorine concentration in saliva until 7 hours after the experiment becomes higher in the sequence of a fluorine varnish, a fluorine gel, and a fluorine tape. However, according to time, the fluorine concentrations of the fluorine gel and fluorine varnish were considerably reduced, and after 24 hours of the experiment, were lower than that of the fluorine tape. Accordingly, the fluorine preparation of the present invention is expected to maintain a suitable fluorine concentration in an oral cavity for a long time due to slow release of the fluorine for a long time. For reference, in FIG. 10, the "APF gel" refers to gel-type fluomulated biodegradation degree were calculated using the following Equation, and the results are shown in Table 5.

Amount of accumulated carbon dioxide:
$$ThCO_2 = M_{TOT} \times C_{TOT} \times (44/12)$$

(where $M_{ror}$ is an amount (g) of a dry solid content of a sample added to a compost is when the test starts, $C_{ror}$ is a ratio (g/g) of an organic carbon included in the dry solid of the sample, and 44 and 12 are a molecular weight of carbon dioxide and an atomic amount of carbon).

Accumulated biodegradation degree: $D_T = \{((CO_2)_T - (CO_2)_B)/ThCO_2\} \times 100$ (where $(CO_2)_T$ is an accumulated amount of carbon dioxide generated from a composting container having a sample; $(CO_2)_B$ is an average value of the accumulated amount of carbon dioxide generated from an inoculums container; and $ThCO_2$ is a theoretical amount of carbon dioxide generated by a sample in a container).

TABLE 5

| Category | $ThCO_2$ (gCO$_2$/ves.) | Biodegradation degree (% on 45$^{th}$ day) | Comparative value at reference (% on 45$^{th}$ day) |
| --- | --- | --- | --- |
| Reference N = 3, average | 8.0910 | 73.5 | — |
| Fourth sample N = 3, average | 2.4967 | 30.0 | 40.8 |
| Seventh sample N = 3, average | 2.2830 | 41.0 | 55.8 |
| Ninth sample N = 3, average | 2.0557 | 54.4 | 74.0 |
| Fourteenth sample N = 3, average | 1.2998 | 74.9 | 101.9 |

The amount of carbon dioxide is a criterion of the biodegradation degree of the polymer by microorganisms in a composting container. Referring to Table 5, the fourth sample had the lowest biodegradation degree, and the fourteenth sample had the highest biodegradation degree.

<5. Clinical Test>

Figure 11:
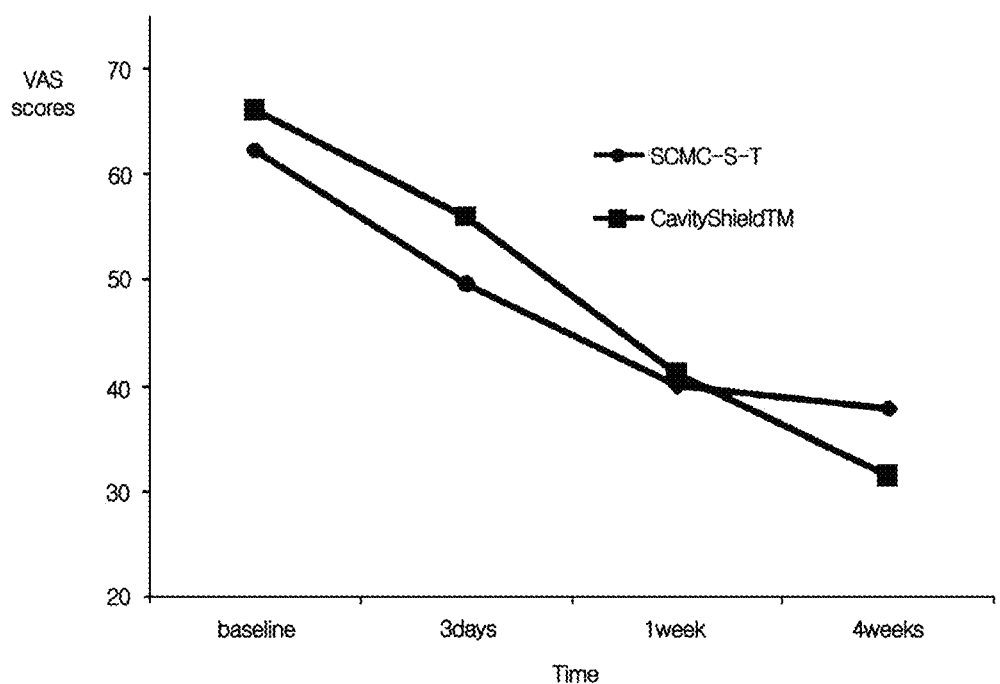
FIG. 11 is a graph showing a degree of pain by time periods, measured by contacting teeth with an ice stick.

A degree of pain was measured by applying a common fluorine varnish product (Cavity Shield) and the fluorine preparation of Example (the tenth sample of Table 3) to cold teeth of university students and contacting the teeth with an ice stick over time, and the results are shown in FIG. 11. In FIG. 11, a VAS point of 0 means that there was no pain, and a VAS point of 100 means that there was very severe pain. In the graph of FIG. 11, "SCMC-S-T" refers to a fluorine preparation used as the tenth sample, and "Cavityshield™" refers to a common fluorine varnish product.

According to the test, there were no significant differences in the conventional fluorine varnish product and the fluorine preparation of Example. It is seen that the fluorine preparation of Example also had an excellent effect.

While the present invention has been described above with reference to Example, Example was merely an example, and those skilled in the art will understand that various modifications and equivalents to Example may be made.

Accordingly, the true scope of the present invention will be made by the accompanying claims.

The present invention may be usefully utilized as an oral medication for a dental application to prevent dental caries, and used as a product for preventing dental caries by a simple method of attaching the product of the present invention to teeth by a user.

While the invention has been shown and described with reference to certain exemplary embodiments thereof, it will be understood by those skilled in the art that various modifications in form and details may be made therein without departing from the spirit and scope of the invention as defined by the appended claims.

The invention claimed is:

1. A method of preparing an adhesive sheet containing fluorine, the method comprising:

mixing 10 to 25 parts by weight of a biodegradable hydrophilic polymer and 100 parts by weight of a solvent to obtain a polymer solution;

adding 1 to 10 parts by weight of a plasticizer to 100 parts by weight of the polymer solution and stirring the resulting polymer solution to which the plasticizer is added;

adding 1 to 10 parts by weight of a fluorine compound and 2 to 20 parts by weight of a pressure-sensitive adhesive to 100 parts by weight of the polymer solution to which the plasticizer is added and stirring the resulting polymer solution to which the fluorine compound and the adhesive are added; and plasticizing the polymer solution to which the plasticizer, fluorine compound and adhesive are added to form the adhesive sheet having a thickness of 10 to 30 μm, wherein the hydrophilic polymer is a mixture of polyvinyl alcohol (PVA) and sodium carboxymethyl cellulose (sodium CMC) configured for slow releasing of fluorine from the adhesive sheet containing fluorine, wherein the hydrophilic polymer has a weight ratio of polyvinyl alcohol to sodium carboxymethyl cellulose of 1:0.3, and wherein the polyvinyl alcohol is completely saponified and has a molecular weight of 1700, and the sodium carboxymethyl cellulose has a viscosity of 400 cp.

2. The method according to claim 1, wherein the fluorine compound is one selected from the group of tin fluoride, sodium monofluorophosphate, and calcium monofluorophosphate.

* * * * *